(12) United States Patent
Muñoz Bonet

(10) Patent No.: US 9,730,614 B2
(45) Date of Patent: Aug. 15, 2017

(54) SYSTEM FOR CONTINUOUS MEASURING, RECORDING AND MONITORING OF THE SPLANCHNIC TISSUE PERFUSION AND THE PULMONARY PHYSIOLOGICAL DEAD SPACE, AND USE THEREOF

(76) Inventor: Juan Ignacio Muñoz Bonet, Valencia (ES)

( * ) Notice: Subject to any disclaimer, the term of this patent is extended or adjusted under 35 U.S.C. 154(b) by 1073 days.

(21) Appl. No.: 13/375,677

(22) PCT Filed: Apr. 15, 2010

(86) PCT No.: PCT/ES2010/070231
§ 371 (c)(1),
(2), (4) Date: Mar. 26, 2012

(87) PCT Pub. No.: WO2010/125215
PCT Pub. Date: Nov. 4, 2010

(65) Prior Publication Data
US 2012/0172683 A1   Jul. 5, 2012

(30) Foreign Application Priority Data
Apr. 29, 2009   (ES) .................. 200901119

(51) Int. Cl.
*A61B 5/1455* (2006.01)
*A61B 5/083* (2006.01)
(Continued)

(52) U.S. Cl.
CPC ........ *A61B 5/0836* (2013.01); *A61B 5/14539* (2013.01); *A61B 5/14551* (2013.01); *A61B 5/4238* (2013.01); *A61B 5/4255* (2013.01)

(58) Field of Classification Search
USPC ................................. 600/310–344
See application file for complete search history.

(56) References Cited

U.S. PATENT DOCUMENTS

2007/0129646 A1   6/2007   Heinonen et al.

FOREIGN PATENT DOCUMENTS

WO   98/01070   1/1998

OTHER PUBLICATIONS

International Search Report issued Jul. 26, 2010 in International (PCT) Application No. PCT/ES2010/070231.
(Continued)

*Primary Examiner* — Eric Winakur
*Assistant Examiner* — Marjan Fardanesh
(74) *Attorney, Agent, or Firm* — Wenderoth, Lind & Ponack, L.L.P.

(57) ABSTRACT

The present invention relates to a new system for measuring, recording and monitoring the splanchnic tissue perfusion and the pulmonary physiological dead space in an automated way, both continuously and intermittently, and in real time, which is easy to manage and generates information easy to interpret. Said system comprises at least four measuring devices of medical parameters, connected to a device receiving, converting, storing, integrating, processing, and allowing the management and display of the data recorded in the measurements and the parameters estimated by the same. For this purpose, said device comprises a specific computer program of estimation of parameters related to the measurement of the splanchnic tissue perfusion and the pulmonary physiological dead space, from the data derived from the measuring devices. Likewise, the present invention is related to the use of a device for measuring, recording and monitoring of the splanchnic tissue perfusion and the pulmonary physiological dead space.

19 Claims, 4 Drawing Sheets

(51) Int. Cl.
*A61B 5/145* (2006.01)
*A61B 5/00* (2006.01)

(56) References Cited

OTHER PUBLICATIONS

International Preliminary Report on Patentability issued Jul. 26, 2010 in International (PCT) Application No. PCT/ES2010/070231.
L. Frey et al., "Monitoring durch Messung des gastrointestinalen Mukosa-pH-Wertes (pHi)," Infusionstherapie and Transfusionmedizin, 1993, vol. 20, No. 5, pp. 248-252.
K. Ewa et al., Base of datos MEDLINE/NLM, "Clinical usefulness of gastric tonometry in anesthesiology and intensive care medicine," Abstract, 2005.
A . Y. Schure et al., Base of datos BIOSIS/BIOSIS, "Assessment of Splanchnic Perfusion using gastric tonometry in children undergoing the Fontan Procedure," Abstract 2002.
P. R. Miller et al., "Threshold values of intramucosal pH and mucosal-arterial CO2 gap during Shock Resuscitation," the Journal of Trauma, Nov. 1998, vol. 45, No. 5, pp. 868-872.

| PgCO$_2$ (mmHg) | PaCO$_2$ (mmHg) | CO$_2$gap (mmHg) | %CO$_2$gap (%) | pHis | pHgap |
|---|---|---|---|---|---|
| 30 | 20 | 10 | 33.3 | 7.22 | 0.18 |
| 40 | 30 | 10 | 25.0 | 7.28 | 0.12 |
| 50 | 40 | 10 | 20.0 | 7.30 | 0.10 |
| 60 | 50 | 10 | 16.7 | 7.32 | 0.08 |
| 70 | 60 | 10 | 14.3 | 7.33 | 0.07 |
| 80 | 70 | 10 | 12.5 | 7.34 | 0.06 |
| 90 | 80 | 10 | 11.1 | 7.35 | 0.05 |
| 100 | 90 | 10 | 10.0 | 7.36 | 0.04 |

Figure 4

SYSTEM FOR CONTINUOUS MEASURING, RECORDING AND MONITORING OF THE SPLANCHNIC TISSUE PERFUSION AND THE PULMONARY PHYSIOLOGICAL DEAD SPACE, AND USE THEREOF

FIELD OF THE INVENTION

The present invention is comprised in the field of medicine, specifically of intensive care and major surgery, particularly for the diagnosis of occult shock.

BACKGROUND OF THE INVENTION

Faced with an inadequate supply of oxygen, the cell uses anaerobic glycolysis in an attempt to maintain the normal cell function, causing an accumulation of lactic acid and the release of hydrogen ions derived from ATP hydrolysis, causing a decrease in the pH of the tissue (see Bibliographic Reference (1)). Thus, the early changes in the pH of the tissue are useful for assessing the oxygenation of that tissue and the status of its microcirculation (2).

In the critically ill patient, when compensatory mechanisms fail to maintain a suitable oxygenation in all tissues, the neurohumoral response of the organism causes a redistribution of the blood flow aimed at preserving the function of "noble organs" such as the brain and the heart, at the expense of decreasing the infusion of "non-vital organs" such as the skin and splanchnic territory (3). Unlike the skin, the splanchnic territory, and particularly the intestinal mucosa, has high metabolic needs that along with certain anatomical characteristics that make it particularly susceptible to hypoxia, account for the intestine being the first organ to be affected in situations of hypoperfusion/hypoxia, and the last one to recover (2, 4). Therefore, the assessment of the tissue oxygenation at this level by monitoring the gastric intramucosal pH (pHi), will allow us to detect these situations early and prevent further worsening thereof, as well as to guarantee full recovery after an obvious shock episode (2, 4, 5).

The pHi can be measured by a microelectrode inserted in the gastric mucosa, but the invasiveness of the method, the impossibility of in vivo recalibration and frequent detachment of the electrode, make it impractical in the clinic (6). Therefore, we turn to the indirect measurement of pHi, based on the principle of tonometry, by which the gases diffuse freely through the tissues. Thus, in 1959 Boda and Murányi (7) made an estimate of the arterial $PCO_2$ in more than 400 children mechanically ventilated for poliomyelitis, using a tonometry probe similar to the current ones, and inserted in the stomach through the nose. Their clinical experience led them to conclude that: 1) The arterial $CO_2$ tension can be estimated with reasonable accuracy with the gastrotonometric method. 2) In patients in severe shock situation the $PCO_2$ in the tonometer may be deceptively high. However, they do not understand the reason for this after fact. These results were subsequently confirmed by Bergofsky (8) by demonstrating that the fluid in the lumen of a hollow organ (urinary bladder, gallbladder, stomach), balances the tension of the gases ($PO_2$ and $PCO_2$) with that of the cells and tissues containing thereof, and these in turn with that of the blood irrigating thereof. And simultaneously also by Dawson (9) that observed in experimental animals how the $PO_2$ and the $PCO_2$ measured in the saline serum instilled in intestinal pouches experienced changes proportional to those of the blood. Therefore, the measurement of the $CO_2$ Pressure in the gas in the lumen of the intestine is equivalent to the $CO_2$ Pressure in the intestinal mucosa (10).

In 1982, Fiddian-Green et al (11) use these findings for postulating that the intestinal mucosa pH can be calculated in an indirect way. This hypothesis is based on two assumptions: 1) The $PCO_2$ tonometrically measured approximates to that of the intestinal mucosa, since the $CO_2$, for its high diffusion capacity, quickly reaches the balance between the tissue and the intraluminal lumen. 2) The bicarbonate concentration in the intestinal mucosa is in balance with that of the intestinal capillary bed, and this in turn, with that of the arterial blood (1). Therefore, the pHi calculation can be performed by a modification of the Henderson-Hasselbalch equation:

$$pHi = 6.1 + \log 10([HCO_3^-]/PgCO_2 * 0.03) \quad \text{Equation 1}$$

Wherein 6.1 is the pK of the $HCO_3^-/CO_2$ system in plasma at 37° C.; $[HCO_3^-]$ is the arterial concentration of bicarbonate (mM/L); $PgCO_2$ is the $PCO_2$ of the tonometry probe set to the equilibrium time; 0.03 is the solubility constant of the $CO_2$ in plasma at 37° C.

Thus, the deceptive $PCO_2$ increases of the stomach in relation to the arterial $PCO_2$, observed by Boda and Murányi in patients in situation of severe shock, would correspond to pHi drops as a result of regional tissue hypoperfusion. Grum et al, in 1984 develop a tonometry probe constituting the basis of the current commercial equipments. Using this equipment in dogs, they observed how the pHi remained constant as long as the blood flow was maintained above a critical value. Below this the pHi decreased. Moreover, these decreases in the pHi were accompanied by decreases in the $O_2$ consumption. In 1990 Antonsson et al (6) validate the technique in an experimental model, by comparison of the tonometrically calculated pHi with that obtained from microelectrodes implanted directly in the mucosa of the stomach.

Classically, 2 other derived parameters have been used. To calculate them the arterial pH values (pHa) are used, obtained with the analysis of an arterial blood sample and the pHi, calculated by equation 1.

$$\text{Difference of pH or pHgap} = pHa - pHi \quad \text{Equation 2}$$

$$\text{Standard intramucosal pH or pHis} = 7.4 - pHgap \quad \text{Equation 3}$$

According to the place where the measurement of the $CO_2$ in the lumen of the digestive tube (PgCO2) is performed, 2 types of measurement are distinguished:

1) Tonometry with $CO_2$ analysis outside the organism: the technique consists of the placement of a nasogastric tube provided with a terminal silicone balloon permeable to $CO_2$ that is left accommodated in the stomach. It is radio-opaque to facilitate its correct location by X-ray (Rx). It is therefore a minimally invasive technique. The analysis requires the extraction of the samples in order to be analysed. There are two types depending on the medium with which the balloon is filled:

A. Tonometry with physiological saline serum (PSS): it is the technique initially used and with which more experience is available. Thus, most of the studies that have evaluated its usefulness have been based on it. The technique requires, however, great user experience to obtain reliable results (12). The process of measuring can be divided in 2 times:

1. Measurement of the $PgCO_2$: prior to the insertion of the catheter a careful purging of the balloon with PSS must be performed, to remove the air it may contain. After its insertion it is filled with 2.5 mL of the same serum, that is maintained over an equilibrium period (30 minutes minimum), that has to be known in case of being of less than 90 minutes, so that the correction is made. When extracting the sample the first mL must be discarded, corresponding to the dead space in the catheter, it must be preserved anaerobically (sealed) and processed immediately to be reliable. The measurement is performed in a standard blood gas analyzer, although there have been objectified important differences between different models, probably as a function of the calibration (it is performed for blood samples, not for PSS), so that each centre has to determine its reference values (2).

2. Calculation of the pHi and related parameters: in order to calculate an arterial blood extraction must be performed. With this sample the arterial pH and $PCO_2$ measurements are obtained in a standard blood gas analyzer. Using these measurements the analyzer itself performs the calculation of the arterial bicarbonate ($HCO_3^-$) that along with the $PgCO_2$ obtained from the tonometry probe allow the calculation of the pHi according to Equation 1. This calculation along with the measurement of the arterial pH, allow the calculation of the pHgap and pHis according to Equations 2 and 3.

A value of pHi<7.31 is generally considered abnormal (13). Therefore, the tonometry technique with saline serum is too cumbersome, requires user experience, is little reproducible and does not provide continuous information. For these reasons, although it has proved to be useful in research studies, it has not been introduced as a usual monitoring technique in critically ill patients. Currently, these probes are no longer marketed.

B. Tonometry with air: to overcome some of the limitations of the tonometry with saline, the Datex-Ohmeda company adapted a capnograph (Tonocap®) that automatically filled the balloon with air, extracting the same periodically (every 10 minutes) to perform the measurements of the $PgCO_2$. The technique was validated by several authors (14-16). Subsequently, an improvement in this equipment, the M-Tone Module of the same manufacturer (currently belonging to the General Electric group) was marketed. These equipments automate the measurements of the $PgCO_2$, but for the calculation of the pHi it is still required to perform intermittent blood extractions that must be analyzed in a standard blood gas analyzer, and the results thereof entered manually in the apparatus. Therefore, although part of the measurement process has been automated, the technique continues to be intermittent and cumbersome.

To mitigate these disadvantages, the use as an indicator of tissue hypoperfusion of a related regional parameter has been proposed, the gastric-arterial $CO_2$ gradient or $CO_2$gap can be calculated as follows:

$$CO_2\text{gap or } P(g-a)CO_2 = PgCO_2 - PaCO_2 \qquad \text{Equation 4}$$

Wherein $PaCO_2$ is the $CO_2$ arterial pressure. This parameter also requires the performing of intermittent blood extractions to obtain the $PaCO_2$. Therefore, the $PCO_2$gap is not measured continuously either. However, the manufacturer has incorporated in the equipment a second capnograph to measure continuously the $CO_2$ end-expiratory pressure ($EtCO_2$), as a way of approximation to the $PaCO_2$, since in normal conditions the $EtCO_2$ is related to the $PaCO_2$ (the difference between both measurements in healthy volunteers is usually of 2 to 5 mmHg). Thus, it performs in an automated and continuous way, the calculation of a new derived parameter: the gradient between the gastric and expiratory $CO_2$:

$$CO_2\text{gap}(et) \text{ or } P(g-Et)CO_2 = PgCO_2 - EtCO_2 \qquad \text{Equation 5}$$

However, the connection between the $PaCO_2$ and the $EtCO_2$ is lost frequently in the critically ill patient (target patient for the implementation of this monitoring). For this reason, the integration of these two parameters has not proven clinical usefulness and the device has fallen into disuse. Still, this equipment and its sampling probes are still marketed by the Datex-Ohmeda company and are available at an international level.

Moreover, the Datex Ohmeda S5 multiparametric system, with M-Tone tonometry module and capnograph for the measurement of the $EtCO_2$, only provides a numerical value of the latest measurement. It does neither represent the data graphically nor does it show trends facilitating the interpretation of the data and assessing its evolution over time.

2) Tonometry with $CO_2$ "in situ" analysis: the measurement of the $CO_2$ in the lumen of the stomach (PgCO2) can be performed "in situ" and in real time by the placement of a fiber optic sensor. This sensor has been developed by The Institute of Chemical Process Development and Control. It has been applied in healthy volunteers and in intensive care patients. However, for this parameter to have clinical usefulness its integration with other systemic variables allowing the calculation of derived regional parameters is necessary. This device offers only this measurement, so it has little clinical usefulness.

As we have seen, the indirect calculation of the pHi or the $CO_2$gap requires intermittent blood extractions to be obtained in order to obtain the bicarbonate or the $PaCO_2$, along with the measurement of the $PgCO_2$. The technique, therefore, is cumbersome and does not provide continuous information, which seriously limits its clinical use. Moreover, the attempt of integration for continuous measuring of the M-Tone Module has not resulted effective so far.

The system described herein overcomes the important limitations of the instruments currently in use, mainly the M-Tone Module of the Datex-Ohmeda company (currently belonging to the General Electric group). Additionally, the present system can estimate in a continuous and automated way the pulmonary physiological dead space in the critically ill patient.

BRIEF DESCRIPTION OF THE DRAWINGS

FIG. 4 depicts a simulation of the output interface (f7) of the device (f) of reception, conversion, storage, integration, processing, management and display of the data recorded in the measurements, allowing the user to view in real time the information input in the device (f) and output from the computer module (f5), in both tabular and graphic form.

DESCRIPTION OF THE INVENTION

Figures 1, 2:
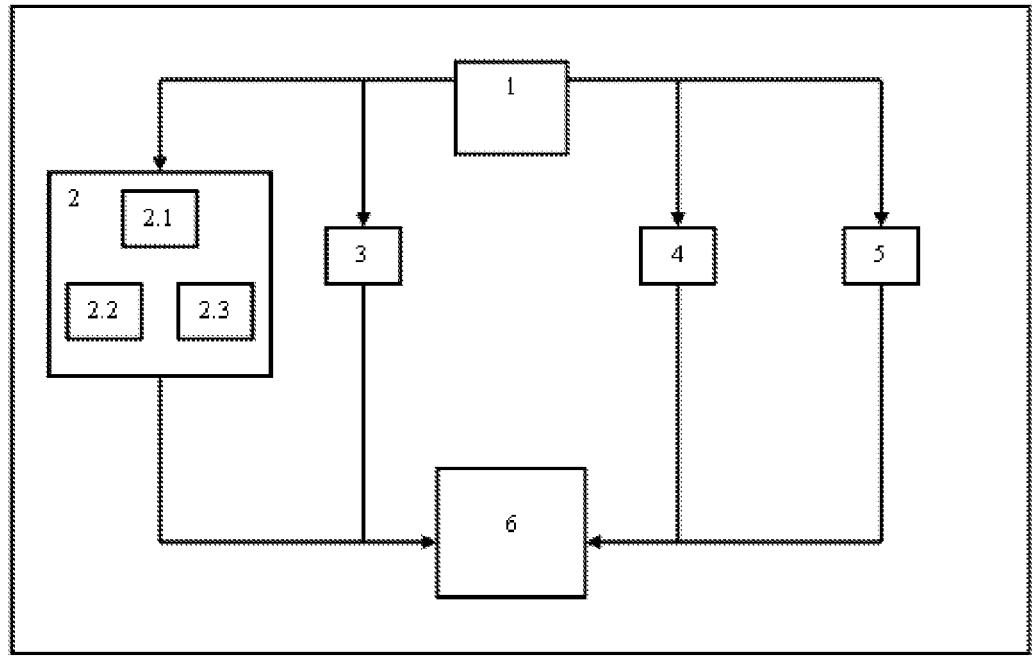
FIG. 1 depicts a scheme of the system for measuring, recording, and monitoring the splanchnic tissue perfusion and the pulmonary physiological dead space in an automated way, both continuously and intermittently, and in real time (pH-Tone instrument).
FIG. 2 depicts a chart showing variation of the %$CO_2$gap, pHis and pHgap at different levels of $PaCO_2$ with a constant $CO_2$gap of 10 mmHg.

The present invention relates to a new system for measuring, recording and monitoring the splanchnic tissue perfusion and the pulmonary physiological dead space in an automated way, both continuously and intermittently, and in real time, which is easy to manage and generates information easy to interpret.

The system object of the present invention comprises at least (FIG. 1):

a) a continuous measuring device of the carbonic anhydride pressure in the lumen of the digestive tube ($PgCO_2$). This device includes a probe the positioning of which can be performed nasogastrically or recto-sigmoidally. The $CO_2$ measurement can be performed by two types of probes:

Probe with terminal silicone balloon permeable to $CO_2$ that is filled with air: the measurement of the $CO_2$ is performed in the apparatus (capnograph) by the extraction, analysis and reintroduction of the gas sample in the balloon, in an intermittent (every 10 minutes) and automated way, as the General Electric M-Tone Module, or another one that might be marketed.

Probe with a fibre optic sensor in its patient end: "continuous measuring in situ", as the developed by The Institute of Chemical Process Development and Control, or other that might be marketed.

b) a standard intermittent measuring device of the arterial pH (pHa) and $CO_2$ arterial pressure ($PaCO_2$) of a blood sample;

c) a continuous measuring device of the $CO_2$ transcutaneous pressure ($PtcCO_2$) consisting of a transcutaneous capnography sensor; and d) a continuous measuring device of the end-expiratory $CO_2$ ($EtCO_2$) consisting of an expiratory air standard capnograph, the probe or sensor of which is connected to the patient's airway;

e) specific connections between the enumerated measuring devices (a, b, c and d) and an f) device. These connections are preferably made in the devices a, c and d through the RS-232 serial ports thereof, and in device b, through its network connection (Ethernet), since its location is usually remote.

f) a device of reception, conversion, storage, integration, processing, management and display of data recorded in the continuous, automated and real-time measurements.

The device (f) of reception, conversion, storage, integration, processing, management and display of data recorded in the measurements comprises at least the following elements:

a computer program module (f1) of reception and storage of the measurements performed with the measuring devices (a, b, c and d), a second specific module (f2) of conversion-normalization of the data received and stored in the module (f1) of reception and storage, a third module (f3) of processing and integration of the data normalized by the normalization module (f2), a fourth program module (f4) of storage of the data processed by the processing module (f3);

a fifth specific module (f5) of automated, continuous and real time estimate of the parameters related to the measurement of the splanchnic tissue perfusion and the pulmonary physiological dead space, from the data derived from the $4^{th}$ storage module (f4) that have been previously processed by the processing module (f3);

an input interface (f6) allowing the user to enter commands in the computer program (f5) of parameter estimate, as well as additional data;

an output interface (f7) allowing the user to view in real time the information input in the device (f) and the output from the computer module (f5), in both tabular and graphic form;

an eighth module (f8) for recording the parameters estimated by the module (f5), for the subsequent recovery and analysis thereof; and an alarm (f9) for checking the operation of the device (f) and the specific connections (e), to detect problems in operating and receiving measurements, and parameters programmable alarm (measurement values exceeded) by the module (f5), independent of that existing in the measuring equipment.

The parameters related to the measurement of the splanchnic tissue perfusion and the pulmonary physiological dead space calculated by the estimate computer program (f5) are the following:

$CO_2$ arterial pressure ($PaCO_2$), which is measured intermittently by the device (b) or is estimated continuously as a function of the $PtcCO_2$;

difference of systemic-regional pH (pHgap), which is estimated as a function of the $PgCO_2$ and the measured $PaCO_2$;

intramucosal pH in the digestive tube (pHi), which is estimated as a function of the pHa, the $PgCO_2$ and the measured $PaCO_2$, standard intramucosal pH (pHis) which is estimated as a function of the normal arterial pH, the $PgCO_2$ and the measured $PaCO_2$, the normal arterial pH being 7.4.

gradient between the pressures of gastric $CO_2$ and arterial $CO_2$ in % (% $CO_2$gap), which is estimated as a function of the $PgCO_2$ and the measured $PaCO_2$;

gradient between the pressures of gastric $CO_2$ and transcutaneous $CO_2$ in % (% $CO_2$gap(tc)), which is estimated as a function of the $PgCO_2$ and the $PtcCO_2$;

difference of transcutaneous-regional pH (pHgap(tc)), which is estimated as a function of the $PgCO_2$ and the $PtcCO_2$;

transcutaneous standard intramucosal pH (pHis(tc)), which is estimated as a function of the normal arterial pH, the $PgCO_2$ and the $PtcCO_2$;

difference of the arterial-respiratory pH (pHgap(a-et)), which is estimated as a function of the measured $PaCO_2$ and the $EtCO_2$;

arterial-respiratory standard pH (pHs(a-et)), which is estimated as a function of the normal arterial pH, the measured $PaCO_2$ and the $EtCO_2$;

pulmonary physiological dead space, $V_D/V_T$, which is estimated as a function of the $PaCO_2$ obtained by the device (b) and the $PECO_2$ obtained by the device (d);

transcutaneous pulmonary dead space ($V_D/V_T$(tc)), which is estimated as a function of the $PtcCO_2$ and the $EtCO_2$;

difference of transcutaneous-expiratory pH (pHgap(tc-et)), which is estimated as a function of the $PtcCO_2$ and the $EtCO_2$; and transcutaneous-expiratory standard pH (pHs(tc-et)), which is estimated as a function of the normal arterial pH, the $PtcCO_2$ and the $EtCO_2$.

Preferably, the measuring device (a) of the carbonic anhydride pressure in the lumen of the digestive tube is the M-Tone Module of the Datex company, which allows the obtainment of the measurement in an automated way every 10 minutes. In a particular embodiment, the device (a) would be constituted by a Datex Ohmeda S5 multiparametric system with an M-Tone tonometry module and tonometry probe output. The information depicting media in this system show the values of $PGCO_2$, $EtCO_2$ and the difference between them $P(g-Et)CO_2$, rounding off decimals, as well as the scale of time between $PgCO_2$ measurements. However, it only provides the numerical value of the latestmeasurement, neither does it represent the data graphically nor does it show trends facilitating the interpretation thereof and assessing its evolution over time.

Preferably, the pHa and $PaCO_2$ values measured by the device (b) of the intermittent blood samples are entered after the analysis either manually through the keyboard or received in an automated way through the Ethernet connection.

The selection of the $CO_2$ transcutaneous pressure measurement ($PtcCO_2$) is due to the fact that it can be performed continuously and bloodless, and it is the one that approximates the closest to the real value of the $CO_2$ arterial Pressure ($PaCO_2$). The measurement of this parameter has not been used previously for the purpose of assessing splanchnic tissue perfusion. Preferably, the transcutaneous capnography sensor of the device (c) is a transcutaneous oxycapnograph for the earlobe. In a particular embodiment, the transcutaneous oxycapnograph for the earlobe is the "Tosca" model of the Radiomether company, comprising 2 sensors, a pulsoxymeter not used in the present invention, and a transcutaneous capnograph (sensor employed in the present invention), since it can be used in patients of any age. Although other manufacturers, such as Sentec, have similar equipment. The Radiomether Tina model can also be used, or any other one.

On its side, the $CO_2$ end-expiratory measurement ($EtCO_2$) has the main purpose of estimating, both intermittently (with the $PaCO_2$ measurement) and continuously (with the $PtcCO_2$ measurement), the pulmonary physiological dead space. The continuous estimate has not been described so far in the literature. This measurement can be obtained with any expiratory air capnograph; there are many manufacturers of this device. Preferably, if the patient is intubated, the $EtCO_2$ measuring probe is attached to the end of the endotracheal tube.

Preferably, the parameter estimate computer program (f5), the device (f) of reception, conversion, storage, integration, processing, management and display of the data recorded in the measurements, performs the following calculations:

Intermittent calculation of parameters for assessment of the splanchnic perfusion: the measurements obtained by the devices (a) and (b) are employed. These calculations have been the ones classically used. However, our invention, unlike other systems, does not employ the usual equations mentioned in the State of the Art section, but simplified equations, in addition to providing a new parameter, the $CO_2$gap in percentage (% $CO_2$gap):

Gastric or sigmoidal intramucosal pH (pHi), from the difference between the pHa and the logarithm of the ratio between the $PgCO_2$ and the $PaCO_2$ measured, expressed by the formula pHi=pHa−log $PgCO_2/PaCO_2$;

Difference of gastric-arterial or systemic-regional pH (pHgap), from the logarithm of the ratio between the $PgCO_2$ and the measured $PaCO_2$, expressed by the formula pHgap=log $PgCO_2/PaCO_2$;

Standard intramucosal pH (pHis), from the difference between the normal arterial pH and the logarithm of the ratio between the $PgCO_2$ and the $PaCO_2$ measured, the normal arterial pH being 7.4, expressed by the formula pHis=7.4−log $PgCO_2/PaCO_2$;

Gradient of gastric-arterial or systemic-regional $CO_2$ in percentage (% $CO_2$gap), from the ratio between: the difference between the $PgCO_2$ and the $PaCO_2$ measured, and the $PgCO_2$, multiplied by 100, expressed by the formula % $CO_2$gap=($PgCO_2−PaCO_2$)*100/$PgCO_2$.

By requiring a blood sample to obtain the arterial pH (pHa) and the $CO_2$ arterial pressure ($PaCO_2$), these parameters can not be calculated continuously, but our invention offers in real time an update of these parameters with the changes in the gastric measurement ($PgCO_2$), using the values of the latest blood sample. The entering of the pH and $PaCO_2$ blood values can be performed manually (without communication) or automatedly. This latter form has the advantage of saving time, and also improves the accuracy when performing data entry in real time, avoiding oversights or delays in the entry thereof.

As it can be seen, with these simplified equations all the regional parameters are calculated using parameters measured directly and not previously calculated (as bicarbonate or pHi). Moreover, the use of constants, which may vary with temperature changes or another one, is eliminated.

Although the $CO_2$ gradient ($CO_2$gap) has been appreciated as the key parameter in the monitoring of the splanchnic perfusion by some authors (17, 18), it has in our opinion a serious disadvantage that has provably caused the tonometric technique to fall into disuse: the interpretation of its values depends on the level of arterial $PCO_2$. Thus, it is not possible to establish a range of normality for this parameter, since this range will vary with the changes in the $PaCO_2$. For this reason, in the present system said parameter has been substituted by the % $CO_2$gap, which like the pHgap and the pHis, takes into account the level of the $PaCO_2$ (FIG. 2).

Calculations for continuous monitoring of the splanchnic perfusion: the measurements obtained by the devices (a) and (c) are used:

$CO_2$ gastric-transcutaneous or transcutaneous-regional gradient in percentage, from the ratio between:

the difference between the $PgCO_2$ and the $PtcCO_2$, and the $PgCO_2$, multiplied by 100, expressed by the formula % $CO_2$gap(tc)=($PgCO_2−PtcCO_2$)*100/$PgCO_2$;

Difference of gastric-transcutaneous or transcutaneous-regional pH, from the logarithm of the ratio between the $PgCO_2$ and the $PtcCO_2$, expressed by the formula pHgap(tc)=log $PgCO_2/PtcCO_2$; and Transcutaneous standard intramucosal pH, from the difference between the normal arterial pH (7.4) and the logarithm of the ratio between the $PgCO_2$ and the $PtcCO_2$, expressed by the formula $$pHis(tc)=7.4-\log PgCO_2/PtcCO_2.$$

The introduction of the normal pH constant allows the obtainment of values in the pH scale easy to interpret.

Intermittent calculation of the pulmonary physiological dead space: the measurements obtained by the devices (b) and (d) are used:

Difference of arterial-expiratory pH, from the logarithm of the ratio between the $PaCO_2$ and the $EtCO_2$, expressed by the formula $$pHgap(a\text{-}et)=\log PaCO_2/EtCO_2; \text{ and}$$

Arterial-expiratory standard pH, from the difference between the normal arterial pH and the logarithm of the ratio between the measured $PaCO_2$ and the $EtCO_2$, expressed by the formula $$pHs(a\text{-}et)=7.4-\log PaCO_2/EtCO_2.$$

It should be noted that our system also makes it possible to perform the exact calculation of the pulmonary physiological dead space $(V_D/V_T)$, expressed by the formula $(PaCO_2-PECO_2)/PaCO_2$. For this purpose, the use of the mean expiratory $CO_2$ $(PECO_2)$ instead of the $EtCO_2$ is required. For measurement thereof, the exhaled $CO_2$ sensor/probe (device d) must be removed from the patient's airway and introduced in a sealed manner in a large bag that receives all the expiratory air from the patient. These measurements are usually performed in the critically ill patient, who is usually intubated, so the expiratory gas collection is simple (the bag is connected to the expiratory gas outlet of the mechanical ventilator). However, it can only be performed when intermittent flow mechanical ventilators (MV) and in controlled mode (CMV) are used, since in SIMV modes, the constant basic flow of the MV will contaminate the sample in the bag. Neither is its measurement possible in the neonatal field due to the systematic use of continuous flow MV at these ages. On the other hand, it is difficult to achieve the sealing of the bag, which can cause inaccurate measurements due to the high diffusivity of $CO_2$. This is the reason why the present invention suggests the parameters pHgap(a-et) and pHs(a-et), that have not been described so far, since they use $EtCO_2$, avoiding the disadvantages of the measurement of the $PECO_2$. These calculations, even though they do not exactly measure the $V_D/V_T$, can be useful to assess the variations thereof in the critically ill patient. Probably, these variations can also be assessed if we substitute the $PECO_2$ by the $EtCO_2$ in the calculation equation of the $V_D/V_T$. This variant of calculation of the $V_D/V_T$ is the one our system usually provides, when the $CO_2$ sensor/probe (device d) is positioned in the patient's airway.

Calculations for the continuous assessment of the pulmonary physiological dead space: the measurements obtained by the devices (c) and (d) are used:

Transcutaneous pulmonary physiological dead space, from the ratio between:
the difference between the $PtcCO_2$ and the $EtCO_2$, and the $PtcCO_2$, expressed by the formula $$V_D/V_T(tc)=(PtcCO_2-EtCO_2)/PtcCO_2;$$

Difference of transcutaneous-expiratory pH, from the logarithm of the ratio between the $PtcCO_2$ and the $EtCO_2$, expressed by the formula $$pHgap(tc\text{-}et)=\log PtcCO_2/EtCO_2; \text{ and}$$

Transcutaneous-expiratory standard pH, from the difference between the normal arterial pH (7.4) and the logarithm of the ratio between the $PtcCO_2$ and the $EtCO_2$, expressed by the formula $$pHs(tc\text{-}et)=7.4-\log PtcCO_2/EtCO_2.$$

For the continuous assessment of the VD/VT (VD/VT (tc)), the use of $EtCO_2$ instead of the $PECO_2$ is proposed herein. For the reasons set forth above, we sacrifice accuracy for convenience. While not providing exact values, we believe that it will allow proper assessment of the changes in this parameter. However, to obtain accurate measurements it is enough to change the position of the $CO_2$ sensor, as we have already discussed.

In another preferred embodiment, the computer program (f5) also estimates also the following parameters related to the continuous measurement of the splanchnic tissue perfusion, from the measurements obtained by the devices (a) and (d):

Gastric-expiratory or expiratory-regional $CO_2$ gradient in percentage, from the ratio between:
the difference between the $PgCO_2$ and the $EtCO_2$, and the $PgCO_2$,
multiplied by 100, expressed by the formula $$\% CO_2gap(et)=(PgCO_2-EtCO_2)*100/PgCO_2;$$

Difference of gastric-expiratory or expiratory-regional pH, from the logarithm of the ratio between the $PgCO_2$ and the $EtCO_2$, expressed by the formula $$pHgap(et)=\log PgCO_2/EtCO_2; \text{ and}$$

expiratory standard intramucosal pH, from the difference between the normal arterial pH (7.4) and the logarithm of the ratio between the $PgCO_2$ and the $EtCO_2$, expressed by the formula $$pHis(et)=7.4-\log PgCO_2/EtCO_2.$$

The parameters described have the advantage, over the classical parameters, of not requiring the extraction and analysis of blood samples for the calculation thereof and, with it, they can be obtained in an automated and continuous way.

Preferably, the device (f) of reception, conversion, storage, integration, processing, management and display of the information is a personal computer.

The present invention relates also to the use of the device described for measuring, recording and monitoring the splanchnic tissue perfusion and the pulmonary physiological dead space in a continuous, real time and automated way. Said measurement, said recording and said monitoring comprise at least the following steps:

1) measuring the $PgCO_2$ by the device (a) of continuous measuring of the carbonic anhydride pressure in the lumen of the digestive tube;
2) measuring the pHa and the $PaCO_2$ on a blood sample by the device (b) of intermittent measuring of the arterial pH and the $CO_2$ arterial pressure;
3) measuring the $PtcCO_2$ by the device (c) of continuous measuring of the $CO_2$ transcutaneous pressure;
4) measuring the $EtCO_2$, by the device (d) of continuous measuring of the end-expiratory $CO_2$;
5) transferring the data of the measurements obtained from the measuring devices (a, b, c and d) to the device (f) of reception, conversion, storage, integration, processing, management and display of said data through the connections (e);

6) converting the data transferred to the device (f) of reception, conversion, storage, integration, processing, management and display of the measurements by the conversion-normalization module (f2), 7) processing and integrating the data converted-normalized in the prior step by the module (f3) of processing and integration of the data, 8) entering commands in the device (f) of reception, conversion, storage, integration, processing, management and display of said data, and estimating and viewing in an automated, continuous and real time way the parameters related to the measurement of the splanchnic tissue perfusion and the pulmonary physiological dead space, by the computer program (f5), the input interface (f6) and the output interface (f7).

Preferably, the measurement of step 1) is performed either in the stomach or in the sigmoidal colon, using the probe with optic fibre sensor or with an already described terminal silicone balloon.

Also preferably, when the measurement of step 1) is carried out in the stomach, the acid secretion of said organ must be inhibited by administering one of the compounds selected from anti-$H_2$ and proton pump inhibitors, to increase the reliability of the measurement.

In a preferred embodiment, in step 3) the device (c) is calibrated "in vivo" at the beginning of the measuring entering a $PaCO_2$ value of a blood sample.

In another preferred embodiment, the $PECO_2$ is measured in step 4) by a large bag wherein the expiratory gas is accumulated and the $CO_2$ Pressure of said gas is determined in said bag by the $CO_2$ probe/sensor of the device d, which is located in the bag in a sealed way.

The scope of application of the monitoring system proposed is exclusively the hospital:

1) Critically ill patients admitted to ICU and resuscitation units: the pHi has shown to be a sensitive but little specific prognostic indicator in the critically ill patient, having shown its usefulness as a multiple organ failure and death predictor in multiple situations, both in the adult and the pediatric patient. Thus, its prognostic usefulness has shown itself to be superior to that of the hemodynamic and systemic oxygenation variables. Its use in interventionist studies to guide the therapy is, however, controversial. Thus, while Gutierrez et al (19) and Ivatury et al (20) observed how the therapy guided by the pHi improved the prognosis of the patients, Gomersall et al (21), did not find any benefit in the group whose therapy was guided by means of the pHi. The limitations of the technique described could explain this deficit. The improvements achieved with the present invention provide the tool necessary to direct the therapy in these patients.

2) The patient undergoing cardiovascular surgery or major surgery, thoracic and abdominal, including liver, intestinal (detection of celiac and mesenteric ischemia) and lung transplant: various studies suggest that the sigmoidal tonometry can be useful to predict the occurrence of ischemic cholitis secondary to tissue hypoxia, main cause of morbidity and mortality after major abdominal vascular surgery. Likewise, the hypoperfusion of the colon detected by tonometry, can be associated to endotoxemia and release of cytokines, which may condition the evolution to MOF and death.

3) Diagnostic assay of celiac and mesenteric symptomatic vascular disease that allows the prediction of the usefulness of surgery.

4) Assessment of the alterations in the ventilation-perfusion in the critically ill patient. These alterations are very frequent in this type of patients, particularly when the pulmonary blood flow decreases (e.g., situations of shock, pulmonary embolism, cardiopulmonary resuscitation), when the alveoli are overdistended by positive pressure ventilation and when the alveolo-capillary interface is destroyed (e.g., emphysema).

The invention described herein presents the following advantages over other systems known in the field of the art:

1. Uses for obtaining the measurements clinical equipment commercially available from different manufacturers. Therefore, the dependence on a single manufacturer is avoided. Moreover, the user will be able to simplify the acquisition of the present system if he uses the measuring equipment available at his Centre. It will also be possible to continue using this equipment independently of the present invention. At the same time, the system will allow all the technological improvements that may be marketed for making measurements of parameters to be incorporated. In this sense, if devices such as Paratrend or other similar ones for continuous measuring of the pHa and the $PaCO_2$ were marketed again, the now intermittent calculations will be able to be carried out continuously.

2. Intermittent monitoring of the splanchnic perfusion:
   In addition to pHi, it provides the calculation of other classical parameters such as pHgap and pHis. These two parameters, although described in the literature, have not been provided by any marketed equipment.
   For the calculation of all the regional parameters their simplified equations are used, only using the parameters measured directly. In this way, interference from previous calculations and changes in the constants of the standard formulae are eliminated.
   Substitutes the calculation of the $CO_2$gap, having serious disadvantages, by a new parameter, % $CO_2$gap, overcoming these limitations.
   For these intermittent calculations, the introduction of measurements derived from blood samples is required. These data can be entered manually (like in other marketed devices) or automatically through the connection with the communications port of the pH and gas analyzer. This latter form has the advantage of saving time for the health care provider, and also improving the accuracy by performing the data entry in real time, avoiding oversights or delays in the entry.
   Although the parameters requiring a blood sample can only be determined intermittently, the present invention offers, in real time, an update of these parameters with the changes of the gastric measurement ($PgCO_2$), using the values of the latest blood sample.

3. Continuous monitoring of the splanchnic perfusion:
   Through the measurements of $PgCO_2$ and $PtcCO_2$ obtained from marketed equipment, the present equipment performs the automated and continuous calculation of new regional parameters, not described so far, of easy clinical interpretation, with ranges of normality fixed and independent of the $CO_2$ blood values. The $PtcCO_2$ had not been used previously for this purpose.
   Provides other regional parameters of continuous measuring not described until now through the integration of the measurements of $PgCO_2$ and $EtCO_2$.
   Improves the health care activity by displaying the information continuously and in real time.
   Decreases the consumption of time by the health care provider and improves the accuracy of the information stored, by carrying out all the functions automatedly.

4. Intermittent and continuous monitoring of the pulmonary physiological dead space: It integrates the measurement of the $CO_2$ exhaled with the $PaCO_2$ for intermittent monitoring, and with the $PtcCO_2$ for continuous monitoring, of the alterations in the pulmonary physiological dead space by calculating the $V_D/V_T$ and the other derived parameters not described so far. This type of monitoring, that allows assessment of alterations in the pulmonary ventilation/perfusion ratio, is currently not provided by any marketed equipment.

5. The information is displayed in tabular and graphic form, easy to be interpreted by clinicians. It assesses the evolution over time by depicting a trends graph.

6. It is provided with an operating alarm system (problem with the reception of the measurements as disconnections, etc.) and a programmable clinical alarm (measurement values exceeded).

7. It saves the information in databases, so that the same can be subsequently recovered.

Therefore, the invention herein described integrates measurements performed by clinical equipment that has not been used previously for this purpose (as the transcutaneous capnograph), to provide in a continuous and automated way new parameters useful for the estimate of the splanchnic perfusion-oxygenation and the pulmonary physiological dead space that are currently not provided by any other marketed system.

ABBREVIATIONS OF THE FIELD OF THE ART

ATP, adenosine triphosphate $CO_2$gap or $P(g-a)CO_2$, gastric-arterial or systemic-regional $CO_2$ gradient ($=PgCO_2-PaCO_2$)

$CO_2$gap(et) or $P(g-Et)CO_2$, gastric-expiratory or expiratory-regional $CO_2$ gradient ($=PgCO_2-EtCO_2$)

% $CO_2$gap, gastric-arterial or systemic-regional $CO_2$ gradient in percentage ($=(PgCO_2-PaCO_2)*100/PgCO_2$)

% $CO_2$gap(et), gastric-expiratory or expiratory-regional $CO_2$ gradient in percentage ($=(PgCO_2-PetCO_2)*100/PgCO_2$)

% $CO_2$gap(tc), gastric-transcutaneous or transcutaneous-regional $CO_2$ gradient in percentage ($=(PgCO_2-PtcCO_2)*100/PgCO_2$)

$EtCO_2$, end-expiratory carbonic anhydride pressure $[HCO_3^-]$, bicarbonate concentration $PaCO_2$, arterial carbonic anhydride pressure $PECO_2$, mean expiratory carbonic anhydride pressure $PgCO_2$, carbonic anhydride pressure in the lumen of the digestive tube (usually in the stomach, but also in the sigmoidal colon)

pHa, arterial pH pHgap, difference of gastric-arterial or systemic-regional pH ($=pHa-pHi$; it can also be calculated by the simplified equation=log $PgCO_2/PaCO_2$)

pHgap(a-et), difference of the arterial-expiratory pH ($=\log PaCO_2/EtCO_2$)

pHgap(et), difference of the gastric-expiratory or expiratory-regional pH ($=\log PgCO_2/EtCO_2$)

pHgap(tc), difference of gastric-transcutaneous or transcutaneous-regional pH ($=\log PgCO_2/PtcCO_2$)

pHgap(tc-et), difference of transcutaneous-expiratory pH ($=\log PtcCO_2/EtCO_2$)

pHi, intramucosal pH in the digestive tube (usually gastric, but also in the sigmoidal colon) ($=6.1+\log 10([HCO3^-PgCO_2*0.03])$; it can also be calculated by the simplified equation=pHa-log $PgCO_2/PaCO_2$)

pHis, standard intramucosal pH ($=7.4-pHgap$; it can also be calculated by the simplified equation=$7.4-\log PgCO_2/PaCO_2$)

pHis(et), expiratory standard intramucosal pH ($=7.4-\log PgCO_2/EtCO_2$)

pHis(tc), transcutaneous standard intramucosal pH ($=7.4-\log PgCO_2/PtcCO_2$)

pHs(a-et), arterial-expiratory standard pH ($=7.4-\log PaCO_2/EtCO_2$)

pHs(tc-et), transcutaneous-expiratory standard pH ($=7.4-\log PtcCO_2/EtCO_2$)

$PaO_2$, oxygen arterial pressure $PtcCO_2$, $CO_2$ transcutaneous pressure

ARDS, acute respiratory distress syndrome

PSS, physiological saline serum $V_D/V_T$, pulmonary physiological dead space ($=(PaCO_2-PECO_2)/PaCO_2$)

$V_D/V_T(tc)$, transcutaneous pulmonary physiological dead space ($=(PtcCO_2-EtCO_2)/PtcCO_2$)

BIBLIOGRAPHY

1. Fiddian-Green R G. Gastric intramucosal pH, tissue oxygenation and acid-base balance. Br. J. Anaesth. 1995; 74: 591-606
2. Fiddian-Green R G. Tonometry: theory and applications. Intensive Care World 1992; 9: 60-65
3. Pinsky M R, Schlichtig R. Regional oxygen delivery in oxygen supply-dependent states. Intensive Care Med. 1990; 16: S169-171
4. Hartmann M, Montgomery A, Jonsson K, et al. Tissue oxygenation in hemorrhagic shock measured as transcutaneous oxygen tension, subcutaneous oxygen tension, and gastrointestinal intramucosal pH in pigs. Crit. Care Med 1991; 19: 205-210
5. Schlichting E, Lyberg T. Monitoring of tissue oxygenation in shock: an experimental study in pigs. Crit. Care Med 1995; 23: 1703-1710
6. Antonson J B, Boyle C C, Kurithoff K L, et al. Validation of tonometric measurement of intramural pH during endotoxemia and mesenteric occlusion in pigs. Am J Physiol 1990; 259: G519-523
7. Boda D, Muranyi L. "Gastrotonometry". An aid to the control of ventilation during artificial respiration. Lancet 1959; 273: 181-182
8. Bergofsky E H. Determination of tissue $O_2$ tensions by hollow visceral tonometers: effect of breathing enriched $O_2$ mixtures. J Crit. Invest 1964; 43: 193-200
9. Dawson A M. Small bowel tonometry: assessment of small gut mucosal oxygen tension in dog and man. Nature 1965; 206: 943-944
10. Fiddian-Green R G, Pittenger G, Whitehouse W M. Back-diffusion of $CO_2$ and its influence on the intramural pH in gastric mucosa. J Surg Res 1982; 33: 39-48
11. Clark C H, Gutierrez G. Gastric intramucosal pH: a noninvasive method for the indirect measurement of tissue oxygenation. Am J Critical Care 1992; 2: 53-60
12. Kolkman J J, Otte J A, Groeneveld B J. Gastrointestinal luminal $PCO_2$ tonometry: an update on physiology, methodology and clinical applications. Br J Anaesth 2000; 84: 74-86
13. Calvo C, Ruza F, López-Herce J, et al. Usefulness of gastric intramucosal pH for monitoring hemodynamic complications in critically ill children. Intensive Care Med 1997 23: 1268-1274
14. Noone R B, Mythen M G, Vaslef S N. In vitro validation of an automated on-line gastrointestinal tonometer (the Tonocap). Crit. Care Med 1997; 25(1S): A137
15. Barry B, Mallick A, Hartley G, et al. Comparison of air tonometry with gastric tonometry using saline and other equilibrating fluids: an in vivo and in vitro study. Intensive Care Med 1998; 24: 777-784

16. Janssens U, Graf J, Koch K C, et al. Gastric tonometry: in vivo comparison of saline and air tonometry in patients with cardiogenic shock. Br J Anaesth 1998; 81: 676-680

17. Schlichtig R, Mehta N, Gayowki T J P, et al. Tissue-arterial PCO2 difference is a better marker of ischemia than intramural pH(pHi) or arterial pH-pHi difference. J Crit. Care 1996; 11: 51-56

18. Vincent J L. Gastric mucosal pH is definitely obsolete. Please tell us more about gastric mucosal PCO2. Crit. Care Med 1998; 26: 1479-1480

19. Gutierrez G, Palizas F, Doglio G, et al. Gastric intramucosal pH as a therapeutic index of tissue oxygenation in critically ill patients. Lancet 1992; 339: 195-199

20. Ivatury R R, Simon R J, Islam S, et al. A prospective randomized study of end points of resuscitation after major trauma: global oxygen transport indices versus organ-specific gastric mucosal pH. J Am Coll Surg 1996; 183: 145-154

21. Gomersall C D, Joint G M, Freebairn R C, et al. Resuscitation of critically ill patients based on the results of gastric tonometry: a prospective, randomized, controlled trial. Crit. Care Med 2000; 28: 607-614

FIGURES

FIG. 1. Scheme of the system for measuring, recording and monitoring the splanchnic tissue perfusion and the pulmonary physiological dead space in an automated way, both continuously and intermittently, and in real time (pH-Tone instrument).

1. Critically ill patient in: intensive care, resuscitation or operating room.
2. Clinical equipment (a) for the measurement of the $PgCO_2$:
    2.1. General Electric M-Tone Module
    2.2. Instrument of the Institute of Chemical Process Development and Control
    2.3. Other
3. Standard blood pH and gas analyzer (b): intermittent measurement of pHa and $PaCO_2$ (multiple manufacturers).
4. Clinical equipment (c) for the measurement of the $PtcCO_2$: Radiomether "Tosca" oxycapnograph, Sentect oxycapnograph or other transcutaneous capnographs.
5. Clinical equipment (d) for the measurement of the $EtCO_2$ and the $PECO_2$ (multiple manufacturers).
6. Device (f) of reception, conversion, storage, integration, processing, management and display of the data recorded in the measurements.

Calculation of Derived Parameters:

measuring device (a)+measuring device (b)=Intermittent monitoring of the splanchnic perfusion.

measuring device (a)+measuring device (c)=Continuous monitoring of the splanchnic perfusion.

measuring device (b)+measuring device (d)=Intermittent monitoring of the pulmonary physiological dead space.

measuring device (c)+measuring device (d)=Continuous monitoring of the pulmonary physiological dead space.

FIG. 2. Variation of the % $CO_2$gap, pHis and pHgap at different levels of $PaCO_2$ with a constant $CO_2$gap of 10 mmHg. As it can be seen, a $CO_2$gap of 10 mmHg is pathological when the arterial $CO_2$ level is normal or low, but not when this is high. Therefore, the interpretation of its values depends on the level of the arterial $PCO_2$ and it is not possible to establish a normal range for this parameter, since it varies with the values of the $PaCO_2$. It is also not possible to compare series of patients since the meaning of a certain value of $CO_2$gap is to be varied as a function of the level of $PaCO_2$ that each patient had. In the inventors' opinion, and contrary to the opinion of other authors (17, 18), this fact seriously limits the usefulness of this parameter, where the % $CO_2$gap, the pHis or the pHgap should be preferably used.

Figure 3:
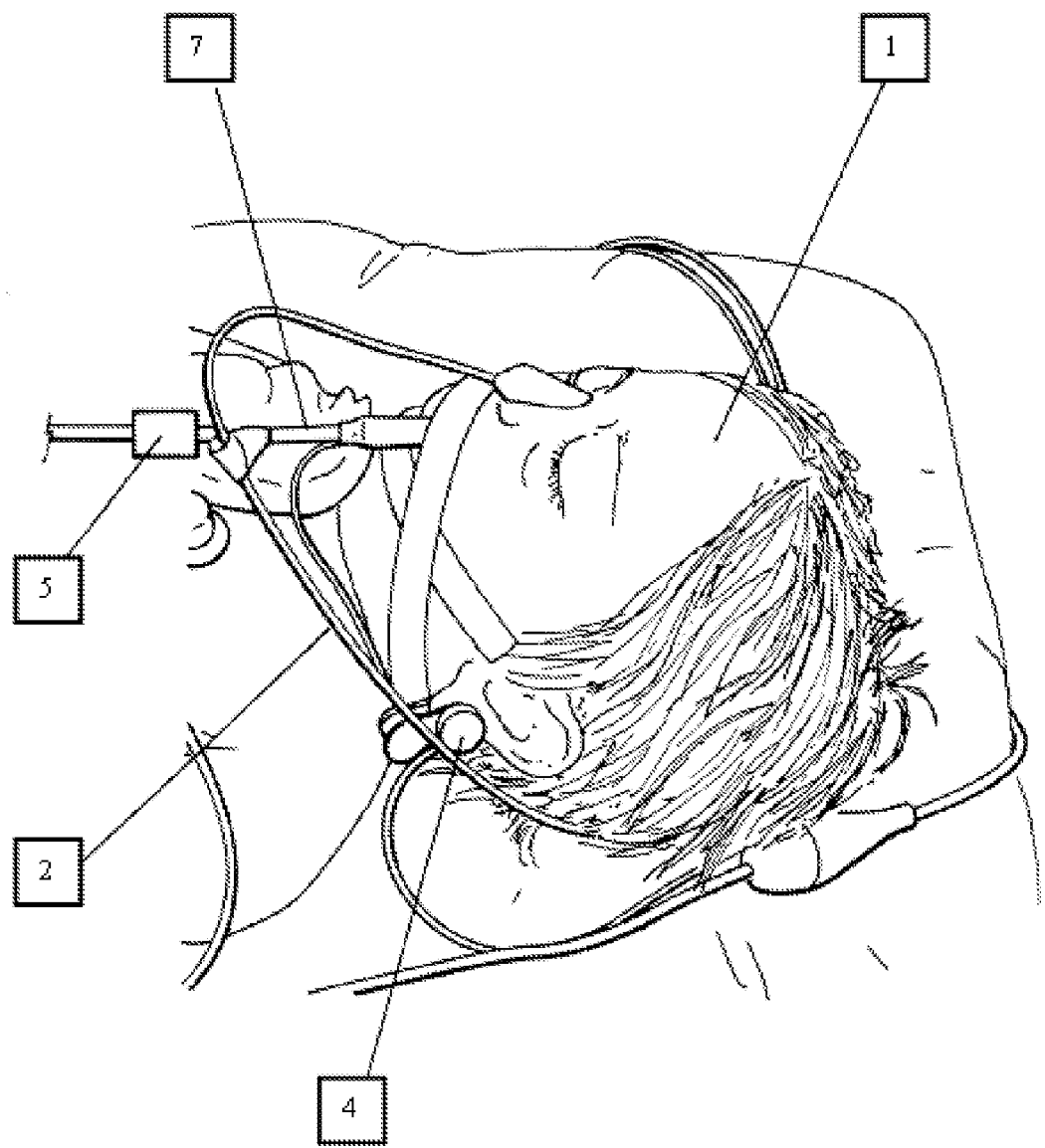
FIG. 3 depicts an illustrative scheme of a patient in intensive care, resuscitation, or operating room with a tonometry probe for the measurement of $PgCO_2$ and a sensor for the earlobe for the measurement of $PtcCO_2$, wherein the probe for the measurement of $EtCO_2$ is found at the end of the endotracheal tube.

FIG. 3. Illustrative scheme of a patient in intensive care, resuscitation or operating room with a tonometry probe for the measurement of $PgCO_2$ and a sensor for the earlobe for the measurement of $PtcCO_2$. The probe for the measurement of $EtCO_2$ is found at the end of the endotracheal tube.

1. Intubated patient.
2. Sonometric probe for the measurement of $PgCO_2$.
4. Sensor for the earlobe for the measurement of $PtcCO_2$.
5. $EtCO_2$ measuring probe.
7. Endotracheal tube (intubation).

Figure 4:
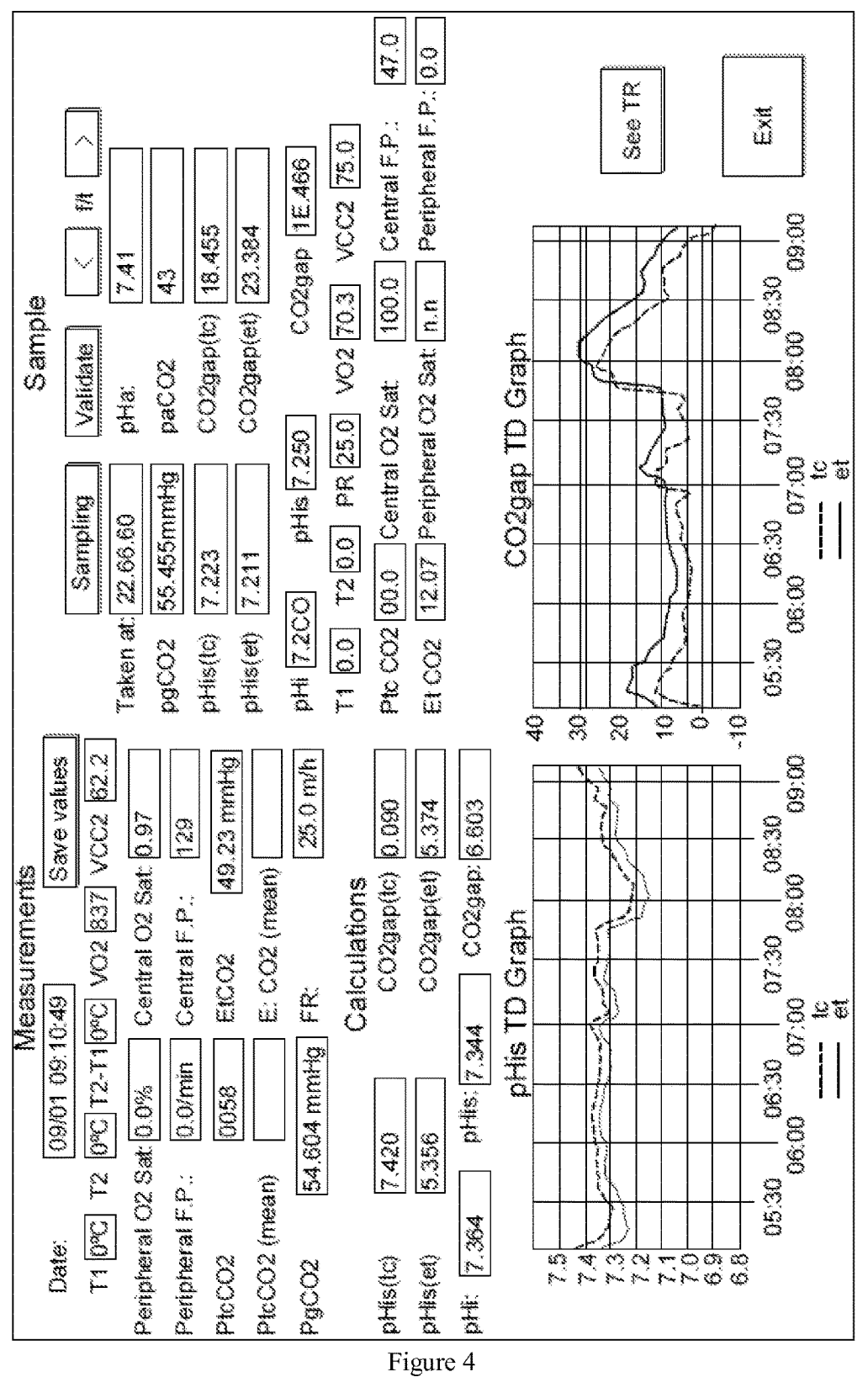

FIG. 4. Simulation of the output interface (f7) of the device (f) of reception, conversion, storage, integration, processing, management and display of the data recorded in the measurements, allowing the user to view in real time the information input in the device (f) and output from the computer module (f5), in both tabular and graphic form. Observe the graphs of continuous monitoring of the pHis and $CO_2$gap, in its two forms of calculation (tc) and (et).

Figure 5:
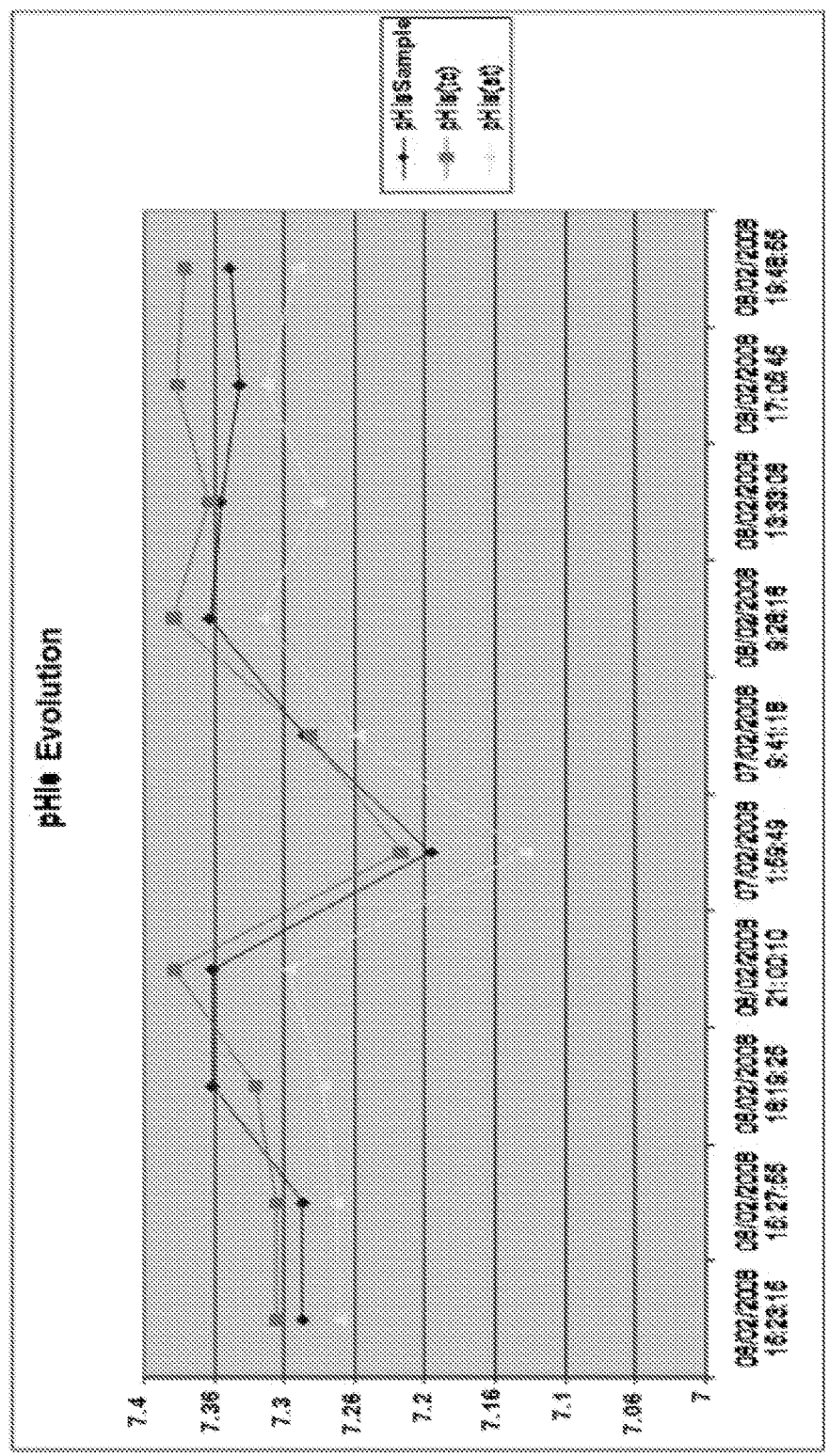
FIG. 5 depicts a graph showing a 48 hours evolution of the standard pHi (pHis) in its three forms of calculation in a patient with ARDS: pHis Sample: calculated intermittently with the measurement of the $PaCO_2$ obtained from a blood sample; pHis(tc): determined in a continuous and automated way with the measurement of the transcutaneous $CO_2$ (present invention); and pHis(et): determined in a continuous and automated way with the measurement of the $CO_2$ exhaled (present invention).

FIG. 5. 48 hours evolution of the standard pHi (pHis) in its three forms of calculation in a patient with ARDS:

pHis Sample: calculated intermittently with the measurement of the $PaCO_2$ obtained from a blood sample.

pHis(tc): determined in a continuous and automated way with the measurement of the transcutaneous $CO_2$ (present invention).

pHis(et): determined in a continuous and automated way with the measurement of the $CO_2$ exhaled (present invention).

Observe the perfect correlation between the pHis calculated with blood sample and transcutaneous sample, and the important differences of both with the pHis(et). These differences can be attributed to variations in the pulmonary ventilation and perfusion. For these measurements, no previous calibration of the $PtcCO_2$ was performed with a measurement of the $PaCO_2$. With this calibration, the correlation between the pHis and the pHis(tc) is still further improved.

The invention claimed is:

1. A system for measuring, recording, and monitoring splanchnic tissue perfusion and pulmonary physiological dead space, comprising:
    a) a continuous measuring device of carbonic anhydride pressure in a lumen of a digestive tube ($PgCO_2$), comprising a probe configured to be positioned nasogastrically or recto-sigmoidally, the probe type for measuring the $CO_2$ being selected from the group consisting of:
        a probe with a terminal silicone balloon permeable to $CO_2$ that is filled with air, which measures $CO_2$ by extraction, analysis, and reintroduction of a gas sample in the balloon every 10 minutes and automatedly; and
        a probe with a optic fiber sensor in its patient end, measuring $CO_2$ in situ and continuously;
    b) a standard intermittent measuring device of the arterial pH, pHa, and $CO_2$ arterial pressure, $PaCO_2$, of a blood sample;

c) a continuous measuring device of $CO_2$ transcutaneous pressure, $PtcCO_2$, consisting of a transcutaneous capnography sensor;

d) a continuous measuring device of end-expiratory $CO_2$, $EtCO_2$, consisting of an expiratory air standard capnograph, the probe or sensor of which is connected in a patient's airway;

e) connections between the measuring devices (a, b, c and d); and f) a device of reception, conversion, storage, integration, processing, management, and display of the data recorded in the measuring devices (a, b, c and d) comprising:

a computer program module (f1) of reception and storage of the measurements performed with the measuring devices (a, b, c and d), a second specific module (f2) of conversion-normalization of data received and stored in the reception and storage module (f1), a third module (f3) of processing and integration of the data converted-normalized by the conversion-normalization module (f2), a fourth program module (f4) of storage of the data processed by the processing module (f3);

a fifth specific module (f5) of automated, continuous, and real time estimate of the following parameters related to the measurement of the splanchnic tissue perfusion and the pulmonary physiological dead space, the data being derived from the fourth storage module (f4) that was previously processed by the processing module (f3):

intramucosal pH in the digestive tube, pHi, which is estimated as a function of the pHa and the $PaCO_2$ obtained by the device (b), and the $PgCO_2$ obtained by the device (a);

difference of gastric-arterial or systemic-regional pH, pHgap, which is estimated as a function of the $PgCO_2$ obtained by the device (a) and the $PaCO_2$ obtained by the device (b);

standard intramucosal pH, pHis, which is estimated as a function of the normal arterial pH, the $PgCO_2$ obtained by the device (a) and the $PaCO_2$ obtained by the device (b), the normal arterial pH being 7.4;

gastric-arterial $CO_2$ gradient in percentage, % $CO_2$gap, which is estimated as a function of the $PgCO_2$ obtained by the device (a) and the $PaCO_2$ obtained by the device (b);

difference of gastric-transcutaneous pH, pHgap(tc), which is estimated as a function of the $PgCO_2$ obtained by the device (a) and the $PtcCO_2$ obtained by the device (c);

transcutaneous standard intramucosal pH, pHis(tc), which is estimated as a function of the normal arterial pH (7.4), the $PgCO_2$ obtained by the device (a) and the $PtcCO_2$ obtained by the device (c);

gastric-transcutaneous $CO_2$ gradient in percentage, % $CO_2$gap(tc), which is estimated as a function of the $PgCO_2$ obtained by the device (a) and the $PtcCO_2$ obtained by the device (c);

difference of arterial-expiratory pH, pHgap(a-et), which is estimated as a function of the $PaCO_2$ obtained by the device (b) and the $EtCO_2$ obtained by the device (d);

arterial-expiratory standard pH, pHs(a-et), which is estimated as a function of the normal arterial pH (7.4), the $PaCO_2$ obtained by the device (b) and the $EtCO_2$ obtained by the device (d);

pulmonary physiological dead space, $V_D/V_T$, which is estimated as a function of the $PaCO_2$ obtained by the device (b) and the $PECO_2$ obtained by the device (d);

transcutaneous pulmonary physiological dead space, $V_D/V_T(tc)$, which is estimated as a function of the $PtcCO_2$ obtained by the device (c) and the $EtCO_2$ obtained by the device (d);

difference of transcutaneous-expiratory pH, pHgap (tc-et), which is estimated as a function of the $PtcCO_2$ obtained by the device (c) and the $EtCO_2$ obtained by the device (d); and transcutaneous-expiratory standard pH, pHs(tc-et), which is estimated as a function of the normal arterial pH, the $PtcCO_2$ obtained by the device (c) and the $EtCO_2$ obtained by the device (d);

an input interface (f6) allowing a user to enter commands in the fifth specific module (f5) of parameter estimation;

an output interface (f7) allowing the user to view in real time the information input in the device (f) and the output from the fifth specific module (f5), in both tabular and graphic form;

a module (f8) of recording the parameters estimated by the fifth specific module (f5), for the subsequent recovery and analysis thereof; and an alarm (f9) for checking the operation of the device (f) and the connections (e), to detect problems in operating and receiving measurements, and parameters programmable alarm (measurement values exceeded) by the fifth specific module (f5), independent of the one existing in the measuring equipment.

2. The system according to claim 1, wherein the probe of the device (a) is configured to be in the stomach or in the recto-sigmoidal colon.

3. The system according to claim 2, wherein the transcutaneous capnography sensor of the device (c) is a transcutaneous oxycapnograph for the earlobe, which can be used in patients of any age.

4. The system according to claim 2, wherein the computer program (f5) of parameter estimates performs the following estimates:

pHi, from the difference between the pHa obtained by the device (b) and the logarithm of the ratio between the $PgCO_2$ obtained by the device (a) and the $PaCO_2$ obtained by the device (b);

pHgap, from the logarithm of the ratio between the $PgCO_2$ obtained by the device (a) and the $PaCO_2$ obtained by the device (b);

pHis, from the difference between the normal arterial pH and the logarithm of the ratio between the $PgCO_2$ obtained by the device (a) and the $PaCO_2$ obtained by the device (b), the normal arterial pH being 7.4, % $CO_2$gap, from the ratio between:

the difference between the $PgCO_2$ obtained by the device (a) and the $PaCO_2$ obtained by the device (b), and the $PgCO_2$, multiplied by 100;

% $CO_2$gap(tc), from the ratio between:

the difference between the $PgCO_2$ obtained by the device (a) and the $PtcCO_2$ obtained by the device (c), and the $PgCO_2$, multiplied by 100;

pHgap(tc), from the logarithm of the ratio between the $PgCO_2$ obtained by the device (a) and the $PtcCO_2$ obtained by the device (c);

pHis(tc), from the difference between the normal arterial pH (7.4) and the logarithm of the ratio between the $PgCO_2$ obtained by the device (a) and the $PtcCO_2$ obtained by the device (c);

pHgap(a-et), from the logarithm of the ratio between the $PaCO_2$ measured with the device (b) and the $EtCO_2$ obtained by the device (d);

pHs(a-et), from the difference between the normal arterial pH (7.4) and the logarithm of the ratio between the $PaCO_2$ measured by the device (b) and the $EtCO_2$ obtained by the device (d);

$V_D/V_T$(tc), from the ratio between:
the difference between the $PtcCO_2$ obtained by the device (c) and the $EtCO_2$ obtained by the device (d), and
the $PtcCO_2$;

pHgap(tc-et), from the logarithm of the ratio between the $PtcCO_2$ obtained by the device (c) and the $EtCO_2$ obtained by the device (d); and pHs(tc-et), from the difference between the normal arterial pH (7.4) and the logarithm of the ratio between the $PtcCO_2$ obtained by the device (c) and the $EtCO_2$ obtained by the device (d).

5. The system according to claim 2, wherein the device (d) further measures the mean $CO_2$ expiratory pressure, $PECO_2$, placing the expiratory $CO_2$ sensor/probe inside a sealed bag placed in the expiratory outlet of the mechanical ventilator, and calculates the pulmonary physiological dead space, $V_D/V_T$, from the ratio between:
the difference between the $PaCO_2$ obtained by the device (b) and the $PECO_2$ obtained by the device (d), and
the $PaCO_2$.

6. The system according to claim 1, wherein the transcutaneous capnography sensor of the device (c) is a transcutaneous oxycapnograph for the earlobe, which can be used in patients of any age.

7. The system according to claim 6, wherein the computer program (f5) of parameter estimates performs the following estimates:
pHi, from the difference between the pHa obtained by the device (b) and the logarithm of the ratio between the $PgCO_2$ obtained by the device (a) and the $PaCO_2$ obtained by the device (b);

pHgap, from the logarithm of the ratio between the $PgCO_2$ obtained by the device (a) and the $PaCO_2$ obtained by the device (b);

pHis, from the difference between the normal arterial pH and the logarithm of the ratio between the $PgCO_2$ obtained by the device (a) and the $PaCO_2$ obtained by the device (b), the normal arterial pH being 7.4, % $CO_2$gap, from the ratio between:
the difference between the $PgCO_2$ obtained by the device (a) and the $PaCO_2$ obtained by the device (b), and
the $PgCO_2$,
multiplied by 100;

% $CO_2$gap(tc), from the ratio between:
the difference between the $PgCO_2$ obtained by the device (a) and the $PtcCO_2$ obtained by the device (c), and
the $PgCO_2$,
multiplied by 100;

pHgap(tc), from the logarithm of the ratio between the $PgCO_2$ obtained by the device (a) and the $PtcCO_2$ obtained by the device (c);

pHis(tc), from the difference between the normal arterial pH (7.4) and the logarithm of the ratio between the $PgCO_2$ obtained by the device (a) and the $PtcCO_2$ obtained by the device (c);

pHgap(a-et), from the logarithm of the ratio between the $PaCO_2$ measured with the device (b) and the $EtCO_2$ obtained by the device (d);

pHs(a-et), from the difference between the normal arterial pH (7.4) and the logarithm of the ratio between the $PaCO_2$ measured by the device (b) and the $EtCO_2$ obtained by the device (d);

$V_D/V_T$(tc), from the ratio between:
the difference between the $PtcCO_2$ obtained by the device (c) and the $EtCO_2$ obtained by the device (d), and
the $PtcCO_2$;

pHgap(tc-et), from the logarithm of the ratio between the $PtcCO_2$ obtained by the device (c) and the $EtCO_2$ obtained by the device (d); and pHs(tc-et), from the difference between the normal arterial pH (7.4) and the logarithm of the ratio between the $PtcCO_2$ obtained by the device (c) and the $EtCO_2$ obtained by the device (d).

8. The system according to claim 6, wherein the device (d) further measures the mean $CO_2$ expiratory pressure, $PECO_2$, placing the expiratory $CO_2$ sensor/probe inside a sealed bag placed in the expiratory outlet of the mechanical ventilator, and calculates the pulmonary physiological dead space, $V_D/V_T$, from the ratio between:
the difference between the $PaCO_2$ obtained by the device (b) and the $PECO_2$ obtained by the device (d), and
the $PaCO_2$.

9. The system according to claim 1, wherein the fifth specific module (f5) of parameter estimates performs the following estimates:
pHi, from the difference between the pHa obtained by the device (b) and the logarithm of the ratio between the $PgCO_2$ obtained by the device (a) and the $PaCO_2$ obtained by the device (b);

pHgap, from the logarithm of the ratio between the $PgCO_2$ obtained by the device (a) and the $PaCO_2$ obtained by the device (b);

pHis, from the difference between the normal arterial pH and the logarithm of the ratio between the $PgCO_2$ obtained by the device (a) and the $PaCO_2$ obtained by the device (b), the normal arterial pH being 7.4, % $CO_2$gap, from the ratio between:
the difference between the $PgCO_2$ obtained by the device (a) and the $PaCO_2$ obtained by the device (b), and
the $PgCO_2$,
multiplied by 100;

% $CO_2$gap(tc), from the ratio between:
the difference between the $PgCO_2$ obtained by the device (a) and the $PtcCO_2$ obtained by the device (c), and
the $PgCO_2$,
multiplied by 100;

pHgap(tc), from the logarithm of the ratio between the $PgCO_2$ obtained by the device (a) and the $PtcCO_2$ obtained by the device (c);

pHis(tc), from the difference between the normal arterial pH (7.4) and the logarithm of the ratio between the $PgCO_2$ obtained by the device (a) and the $PtcCO_2$ obtained by the device (c);

pHgap(a-et), from the logarithm of the ratio between the $PaCO_2$ measured with the device (b) and the $EtCO_2$ obtained by the device (d);

pHs(a-et), from the difference between the normal arterial pH (7.4) and the logarithm of the ratio between the $PaCO_2$ measured by the device (b) and the $EtCO_2$ obtained by the device (d);

$V_D/V_T(tc)$, from the ratio between:
the difference between the $PtcCO_2$ obtained by the device (c) and the $EtCO_2$ obtained by the device (d), and the $PtcCO_2$;
pHgap(tc-et), from the logarithm of the ratio between the $PtcCO_2$ obtained by the device (c) and the $EtCO_2$ obtained by the device (d); and
pHs(tc-et), from the difference between the normal arterial pH (7.4) and the logarithm of the ratio between the $PtcCO_2$ obtained by the device (c) and the $EtCO_2$ obtained by the device (d).

10. The system according to claim 9, wherein the device (d) further measures the mean $CO_2$ expiratory pressure, $PECO_2$, placing the expiratory $CO_2$ sensor/probe inside a sealed bag placed in the expiratory outlet of the mechanical ventilator, and calculates the pulmonary physiological dead space, $V_D/V_T$, from the ratio between:
the difference between the $PaCO_2$ obtained by the device (b) and the $PECO_2$ obtained by the device (d), and the $PaCO_2$.

11. The system according to claim 1, wherein the device (d) further measures mean $CO_2$ expiratory pressure, $PECO_2$, the expiratory $CO_2$ sensor/probe configured to be placed inside a sealed bag placed in the expiratory outlet of the mechanical ventilator, and calculates the pulmonary physiological dead space, $V_D/V_T$, from the ratio between:
the difference between the $PaCO_2$ obtained by the device (b) and the $PECO_2$ obtained by the device (d), and the $PaCO_2$.

12. The system according to claim 1, wherein the connections (e) in the devices (a), (c) and (d) are made through the RS-232 serial ports, and the device (b) through its ethernet network connection.

13. The system according to claim 1, wherein the fifth specific module (f5) further estimates the following parameters related to the continuous measurement of the splanchnic tissue perfusion:
gastric-expiratory $CO_2$ gradient in percentage, %$CO_2$gap (et), from the ratio between:
the difference between the $PgCO_2$ obtained by the device (a) and the $EtCO_2$ obtained by the device (d), and the $PgCO_2$,
multiplied by 100;
difference of expiratory-regional pH, pHgap(et), from the logarithm of the ratio between the $PgCO_2$ obtained by the device (a) and the $EtCO_2$ obtained by the device (d); and
expiratory standard intramucosal pH, pHis(et), from the difference between the normal arterial pH and the logarithm of the ratio between the $PgCO_2$ obtained by the device (a) and the $EtCO_2$ obtained by the device (d), the normal arterial pH being 7.4.

14. The system according to claim 1, wherein the device (f) of reception, conversion, storage, integration, processing, management and display of the information is a personal computer.

15. A method for measuring, recording or monitoring the splanchnic tissue perfusion and the pulmonary physiological dead space in real time and in an automated way, either intermittently or continuously depending on the parameter to be measured, using the system defined in claim 1, wherein the method comprises the following steps:
1) measuring the $PgCO_2$ by the device (a) of continuous or automated measuring, every 10 minutes, of the carbonic anhydride pressure in the lumen of the digestive tube;
2) measuring the pHa and the $PaCO_2$ in a blood sample by the device (b) of intermittent measuring of the arterial pH and the $CO_2$ arterial pressure;
3) measuring the $PtcCO_2$ by the device (c) of continuous measuring of the $CO_2$ transcutaneous pressure;
4) measuring the $EtCO_2$, by the device (d) of continuous measuring of the end-expiratory $CO_2$;
5) transferring the data of the measurements obtained from the measuring devices (a, b, c and d) to the device (f) of reception, conversion, storage, integration, processing, management and display of said data through the connections (e);
6) converting-normalizing the data transferred to the device (f) of reception, conversion, storage, integration, processing, management and display of the measurements by the conversion-normalization module (f2),
7) processing and integrating the data converted-normalized in the prior step by the processing and integration module (f3),
8) entering commands in the device (f) of reception, conversion, storage, integration, processing, management and display of said data, and estimating and viewing in an automated, continuous and real time way the parameters related to the measurement of the splanchnic tissue perfusion and the pulmonary physiological dead space, by the computer program (f5), the input interface (f6) and the output interface (f7).

16. The method according to claim 15, wherein the measurement of step 1) is performed in one of the organs selected from the group consisting of the stomach and the recto-sigmoidal colon.

17. The method according to claim 16, wherein when the measurement of step 1) is carried out in the stomach, the acid secretion of said organ is inhibited by the administration of one of the compounds selected from anti-$H_2$ or proton pump inhibitors, to increase the reliability of the measurement.

18. The method according to claim 15, wherein in step 3) the device (c) is calibrated in vivo at the beginning of the measuring entering a $PaCO_2$ value of a blood sample.

19. The method according to claim 15, wherein in step 4) the $PECO_2$ is measured by the positioning of the expiratory $CO_2$ sensor/probe in a large sealed bag connected to the expiratory outlet of the mechanical ventilator, wherein the expiratory gas is accumulated, and the Pressure of said gas in said bag is determine.

* * * * *